United States Patent [19]

Hoelderich et al.

[11] Patent Number: 4,665,252

[45] Date of Patent: May 12, 1987

[54] PREPARATION OF ALKYLBENZENES

[75] Inventors: Wolfgang Hoelderich, Frankenthal; Rolf Fischer, Heidelberg; Wolf D. Mross, Frankenthal; Frank-Friedrich Pape, Ludwigshafen, all of Fed. Rep. of Germany

[73] Assignee: BASF Aktiengesellschaft, Ludwigshafen, Fed. Rep. of Germany

[21] Appl. No.: 840,898

[22] Filed: Mar. 18, 1986

[30] Foreign Application Priority Data

Apr. 16, 1985 [DE] Fed. Rep. of Germany ....... 3513569

[51] Int. Cl.$^4$ .............................................. C07C 5/32
[52] U.S. Cl. .................................... 585/431; 585/432
[58] Field of Search ................................ 585/431, 432

[56] References Cited

U.S. PATENT DOCUMENTS

| 2,976,331 | 7/1961 | Kimberlin et al. | 585/257 |
| 3,312,635 | 3/1967 | Liquori | 502/315 |
| 4,300,010 | 4/1981 | Cihonski | 585/434 |
| 4,429,175 | 3/1984 | Cihonski | 585/433 |

FOREIGN PATENT DOCUMENTS

| 22297 | 2/1981 | European Pat. Off. |
| 77289 | 5/1983 | European Pat. Off. |

OTHER PUBLICATIONS

Bulletin of the Chem. Society of Japan, vol. 51 (1978), pp. 3641–3642.

Primary Examiner—Curtis R. Davis
Attorney, Agent, or Firm—John H. Shurtleff

[57] ABSTRACT

Alkylbenzenes are prepared by converting an alkyl-, alkylidene- or alkenylcyclohexene or an alkyl- or alkenylcyclohexadiene in the presence of an acidic zeolite catalyst of the pentasil type, in the gas phase or liquid phase.

15 Claims, No Drawings

PREPARATION OF ALKYLBENZENES

The present invention relates to a process for the preparation of alkylbenzenes by converting an alkyl-, alkylidene- or alkenylcyclohexene or an alkyl- or alkenylcyclohexadiene over a catalyst.

It is known that vinylcyclohexene can be converted to ethylbenzene over a noble metal catalyst, such as palladium, platinum, ruthenium or iridium on a basic carrier (European Patent 22,297). It is also known that limonene can be converted to a mixture of p-cymene, trans-p-menthane and 3-p-menthene over a supported catalyst containing nickel oxide and molybdenum oxide, at from 200° to 350° C. (U.S. Pat. No. 3,312,635). Instead of nickel oxide and molybdenum oxide catalysts, magnesium oxide, calcium oxide or lanthanum oxide can also be used in the presence of hydrogen (Bull. Chem. Soc. Jap. 51 (1978), 3641–3642). p-Cymene is also obtainable by converting limonene, α-pinene, β-pinene or limonene-containing terpentine oil over alkali metal carbonates on carriers (European Patent 77,289).

In all of the cases mentioned, the catalysts used are those in which either the carrier or the active components on the carrier are basic substances, such as metal oxides or metal carbonates.

U.S. Pat. No. 2,976,331 describes the conversion of cyclic olefins to aromatics, over metal aluminum silicates having pore diameters of from 10 to $13.10^{-10}$ m. The selectivity of these coarse-pore zeolites is extremely poor.

U.S. Pat. Nos. 4,300,010 and 4,429,175 state that vinylcyclohexene can be dehydrogenated to ethylbenzene if a non-acidic, palladium-doped aluminosilicate zeolite having a pore diameter of less than $5.10^{-10}$ m, eg. zeolite A, is used as the catalyst, and the reaction is carried out in the presence of molecular oxygen. In this process, the zeolite serves as a carrier for the active component palladium. The precondition for high activity and selectivity is an expensive stepwise calcination of the catalyst, where calcination is carried out first in the presence of molecular oxygen and then in a hydrogen atmosphere or in an atmosphere containing nonaromatic $C_1$–$C_{10}$-hydrocarbons.

It is an object of the present invention to provide a catalyst which permits cyclohexenes or cyclohexadienes substituted in various ways to be converted to alkylbenzenes. The catalyst should be readily available, have a long life and high activity, be easy to regenerate and ensure high conversions with good selectivity.

We have found that this object is achieved, and that alkylbenzenes can advantageously be prepared by converting an alkylcyclohexene, an alkylidenecyclohexene and/or an alkenylcyclohexene or an alkyl- or alkenylcyclohexadiene in the presence of a catalyst, if an acidic zeolite catalyst of the pentasil type, i.e. a zeolite having the pentasil structure, is used and the reaction is carried out in the gas phase or liquid phase.

In the novel process, the requirements set at the outset with regard to the catalyst are substantially met. In view of the prior art, which states that the conversion can be carried out over non-acidic catalysts, the success of the process is particularly surprising. Instead of fine-pore aluminosilicate zeolites, medium-pore zeolites of the pentasil type are used. The dehydrogenation can be carried out in the absence of oxygen, making the industrial procedure substantially safer.

Where vinylcyclohexene is used as the starting material for the preparation of ethylbenzene, the reaction can be represented by the following equation:

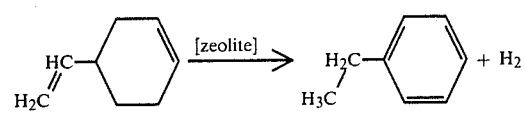

Examples of suitable starting materials for the conversion according to the invention are alkyl-substituted cyclohexenes of cyclohexadienes, the alkyl substituent being straight-chain or branched and of 1 to 10, preferably 1 to 5, carbon atoms. Alkyl is preferably methyl, ethyl, propyl, isopropyl, n-butyl, tert-butyl, n-pentyl or isopentyl.

Alkylidenecyclohexenes, eg. 4-methylene or 4-isopropylidenecyclohex-1-ene can also be converted to alkylbenzenes.

The novel process is particularly useful for the conversion of cyclohexene and/or cyclohexadienes which are substituted at one carbon atom by a branched or straight-chain alkenyl radical of 2 to 10, in particular 2 to 8, preferably 2 to 4, carbon atoms and may carry a low molecular weight alkyl group of 1 to 4 carbon atoms on another carbon atom, eg. 4-allyl-, 4-pentenyl-, 1-methyl-4-hexenyl-, 1-isopropyl-4-vinyl-, 3-vinyl- or 2-allylcyclohex-1-ene, 5-vinylcyclohexa-1,3-diene or 3-isobutenyl-6-methylcyclohexa-1,4-diene.

In particular, alkenylcyclohexenes of the general formula (I)

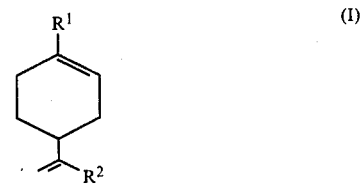

where $R^1$ and $R^2$ independently of one another are each hydrogen or a low molecular weight alkyl group of 1 to 4 carbon atoms, eg. 1-methyl-4-vinyl- or 4-vinyl-cyclohex-1-ene, can be readily converted to alkylbenzenes of the formula (II)

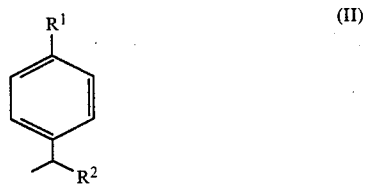

where $R^1$ and $R^2$ have the above meanings.

Using the novel process, it is possible to convert monocyclic unsaturated terpenes, for example sesquiterpenes, such as bisabolene or zingiberene. Particularly advantageous is the conversion of monocyclic monoterpenes, such as $\Delta^3$-menthene, 3-isopropyl-6-methylenecyclohex-1-ene, α-terpinene and in particular α-limonene to p-cymene. Instead of limonene, it is also possible to use the isomeric bicyclic monoterpenes in which the middle carbon atom of the isopropyl group is bonded to a second carbon atom of the cyclohexene ring, eg. α-pinene, β-pinene or $\Delta^3$-carene. p-Cymene may also advantageously be prepared using a mixture of isomeric terpenes of the empirical formula $C_{10}H_{16}$, or using terpentine oil.

The conversion of the starting materials to alkylbenzenes is carried out in the liquid phase at from 30° to 300° C., preferably from 50° to 200° C., or advantageously in the gas phase at from 100° to 500° C., in particular from 200° to 400° C., preferably from 250° to 300° C. The space velocity (WHSV) is from 0.1 to 20, preferably from 0.5 to 5, g of starting material per g of catalyst per hour.

The reaction can be carried out in the presence of an inert solvent, which may be used in an amount of from 20 to 80% by weight, based on the starting material. As a rule, however, the starting materials are reacted directly, without the addition of a solvent.

Acidic zeolite catalyst of the pentasil type are employed as catalysts for the reaction according to the invention. Zeolites are crystalline aluminosilicates which have a highly ordered structure comprising a rigid three-dimensional network of $SiO_4$ and $AlO_4$ tetrahedra which are connected by common oxygen atoms. The ratio of the Si and Al atoms to oxygen is 1:2. The electrovalency of the aluminum-containing tetrahedra is compensated by the inclusion of cations in the crystal, for example an alkali metal or hydrogen ion. Cation exchange is possible; before dehydration by drying or calcination, the voids between the tetrahedra are occupied by water molecules. The zeolites can contain other trivalent elements, such as B, Ga, Fe or Cr, in place of the aluminum, and other tetravalent elements, such as Ge, instead of the silicon.

These zeolites may have different chemical compositions, and may be aluminosilicate, borosilicate, iron silicate, gallium silicate, chromium silicate, arsenic silicate and bismuth silicate zeolites or mixtures of these, or aluminogermanate, borogermanate, gallium germanate or iron germanate zeolites or mixtures of these. Aluminosilicate, borosilicate and iron silicate zeolites of the pentasil type and the isotactic zeolites described in German Laid-Open Application DOS 3,006,471 are particularly preferred.

The aluminosilicate zeolite can be prepared, for example, from an aluminum compound, preferably Al(OH)$_3$ or $Al_2(SO_4)_3$, and a silicon component, preferably highly disperse silica, in aqueous amine solution, in particular in 1,6-hexanediamine, 1,3-propanediamine or triethylenetetramine solution, with or without the addition of an alkali or an alkaline earth, at from 100° to 220° C., under autogenous pressure. The resulting aluminosilicate zeolite has an $SiO_2/Al_2O_3$ ratio of from 10 to 40000, depending on the amounts of starting materials chosen. The aluminosilicate zeolites can also be prepared in an ether medium, such as diethylene glycol dimethyl ether, in an alcoholic medium, such as methanol or 1,4-butanediol or in water.

The borosilicate zeolite can be synthesized, for example, at from 90° to 200° C. under autogenous pressure by reacting a boron compound, eg. $H_3BO_3$, with a silicon compound, preferably highly disperse silica, in aqueous amine solution, in particular in 1,6-hexanediamine, 1,3-propanediamine or triethylenetetramine solution, with or without the addition of an alkali or alkaline earth. In this reaction, an ether solution, for example one containing diethylene glycol dimethyl ether, or an alcoholic solution, for example one containing 1,6-hexanediol, can be used as the solvent, instead of an aqueous amine solution.

The iron silicate zeolite is obtained, for example, from an iron compound, preferably $Fe_2(SO_4)_3$, and a silicon compound, preferably highly disperse silica in this case too, in aqueous amine solution, in particular 1,6-hexanediamine, with or without the addition of an alkali or alkaline earth, at from 100° to 200° C., under autogenous pressure.

The aluminosilicate, borosilicate and iron silicate zeolites prepared in this manner are isolated, dried at from 100° to 160° C., preferably 110° C., and calcined at from 450° to 550° C., preferably 500° C., and can then be molded with a binder in a weight ratio of from 90:10 to 40:60 to give extrudates or tablets. Suitable binders are various aluminas, preferably boehmite, amorphous aluminosilicates having an $SiO_2/Al_2O_3$ ratio of from 25:75 to 95:5, preferably 75:25, silica, preferably highly disperse $SiO_2$, mixtures of highly disperse $SiO_2$ and highly disperse $Al_2O_3$, highly disperse $TiO_2$ and clay. After the molding procedure, the extrudates or tablets are dried at 110° C. for 16 hours and calcined at 500° C. for 16 hours. Such catalysts can be particularly advantageously prepared by molding the isolated aluminosilicate, borosilicate or iron silicate zeolite directly after the drying procedure and subjecting it to calcination only after the molding procedure. The catalyst extrudates can be milled and screened to give fluidizable material having a particle size of, for example from 0.1 to 0.6 mm. However, the aluminosilicate, borosilicate and iron silicate zeolites may also be used in pure form without a binder, as extrudates or tablets. This molding procedure is carried out by adding extrudation or peptization assistants, eg. hexaethylcellulose, potato starch, formic acid, acetic acid, oxalic acid, nitric acid, ammonia, an amine, a silicoester, graphite or a mixture of these.

If, because of its method of preparation, the zeolite is obtained not in the catalytically preferred acidic H form but in the Na form, the latter can be converted completely or partially to the desired H form by ion exchange with ammonium ions followed by calcination, or by treatment with an acid. The zeolites may also be modified in a variety of ways in order to increase the selectivity, the time-on-stream and the number of possible regenerations. In a suitable method of modification, for example, the unmolded or molded zeolite is subjected to ion exchange with, or impregnated with, alkali metals such as Na (unless the alkali metal form of the zeolite is obtained in the synthesis), alkaline earth metals, such as Ca or Mg, or earth metals, such as B or Tl. The zeolites are particularly advantageously doped with transition metals, such as Mo, W, Fe, Zn, Cu or Ni, with noble metals, such as Pd or Pt, and with rare earth metals, such as Ce or La.

In practice, such modified catalysts are prepared, for example, by a method in which the molded pentasil zeolite is initially taken in a riser tube and, for example, an aqueous or ammoniacal solution of a halide or nitrate of the metals described above is passed over the said zeolite at from 20° to 100° C. Ion exchange of this type can be carried out on, for example, the hydrogen, ammonium or alkali metal form of the pentasil zeolite. The metal can also be applied to the zeolite by, for example, impregnating the zeolite material with, for example, a halide, a nitrate, or an oxide of the metals described above, in aqueous, alcoholic or ammoniacal solution. Both ion exchange and impregnation are followed by one or more drying procedures and, if desired, repeated calcination.

The specific procedure is, for example, as follows: nickel nitrate, $Ni(NO_3)_2.6H_2O$ or $Ce(NO_3)_3.6H_2O$ is dissolved in water, and this solution is then used to impregnate the pentasil zeolite which is unextruded or has been extruded with or without a binder, impregnation being carried out for a particular time, ie. about 30 minutes. The supernatent solution is freed from water in a rotary evaporator, after which the impregnated zeolite is dried at about 150° C. and calcined at about 550° C. This impregnation process can, if necessary, be carried out several times in succession in order to obtain the desired metal content.

It is also possible, for example, to prepare an ammoniacal $Pd(NO_3)_2$ solution and to suspend the pure zeolite powder in this solution at from 40° to 100° C. for about 24 hours while stirring. After being filtered off, dried at about 150° C. and calcined at about 500° C., the zeolite material obtained in this manner can be further processed with or without a binder to give extrudates, pellets or fluidizable material.

Ion exchange with the zeolite in the H form can be effected by a procedure in which the zeolite, in the form of extrudates or pellets, is initially taken in a column, and, for example, an ammoniacal $Pd(NO_3)_2$ solution is circulated over the said zeolite at slightly elevated temperatures of from 30° to 80° C. for from 15 to 20 hours. The zeolite is then washed thoroughly with water, dried at about 150° C. and calcined at about 550° C.

In the case of some metal-doped zeolites, aftertreatment with hydrogen is advantageous.

In another possible method of modification, for example, the zeolite material, either molded or unmolded, is subjected to a treatment with an acid, such as hydrochloric acid, hydrofluoric acid or phosphoric acid and/or with steam. This is advantageously done by refluxing the zeolite powder, before it is molded, with from 0.001 to 2N, preferably from 0.05 to 0.5N hydrofluoric acid for from 1 to 3 hours. The product is filtered off, washed thoroughly, dried at from 100° to 160° C. and then calcined at from 400° to 550° C. It may also be advantageous to treat the zeolite with hydrochloric acid after the zeolite has been molded with a binder. In this case, the zeolite is treated with a 3-25, in particular 12-20, % strength hydrochloric acid, for example for from 1 to 3 hours at from 60° to 80° C., after which it is washed thoroughly, dried at from 100° to 160° C. and calcined at from 400° to 550° C. The zeolites may furthermore be modified by applying a phosphorus compound, such as trimethyl phosphate.

After any deactivation of the zeolite catalysts, which may occur in the process of the invention as a result of coking, these catalysts can be regenerated in a simple manner by removing the coke deposit with air or an air/$N_2$ mixture at from 400° to 550° C., preferably 500° C., so that they regain their initial activity. By precoking, the activity of the catalyst can furthermore be adjusted to obtain optimum selectivity with respect to the desired reaction product. The product composition and life of the catalyst can be influenced by carrying out the reaction in the presence of gases such as hydrogen, nitrogen and steam. In general, the catalysts are employed alternatively in the form of 2-4 mm extrudates, tablets having a diameter of from 3 to 5 mm or powders having particle sizes of from 0.3 to 0.5 mm, or as fluidizable catalysts of from 0.1 to 0.6 mm.

The novel process can be carried out batchwise or continuously under atmospheric or superatmospheric pressure by a method conventionally employed for this purpose, for example in a continuous-flow reactor, a stirred kettle or a fluidized-bed reactor.

When the reaction is complete, the resulting alkylbenzenes are isolated from the reaction mixture by a conventional technique, for example by distillation, and unconverted starting materials are, if required, separated off and reused for the reaction according to the invention.

Compounds which are readily obtainable chemically, such as vinylcyclohexane, which is formed, for example, by the dimerization of butadiene, or such as limonene or $\alpha$- or $\beta$-pinene, which are present in many plants or are obtained in substantial amounts as by-products in various industrial processes, can be converted to important intermediates by the novel process. For example, p-cymene is used for the preparation of p-cresol. Styrene, which is used, for example, for the synthesis of polystyrene, can be obtained by dehydrogenating ethylbenzene.

EXAMPLES 1 TO 12

The reaction was carried out as follows: limonene, $\alpha$- or $\beta$-pinene or vinylcyclohexene was employed in a tube reactor under isothermal conditions and passed in the gas phase over a zeolite catalyst at from 200° to 300° C. The reaction products obtained were worked up by distillation and characterized by their boiling point, refractive index and NMR spectra.

Quantitative determination of the reaction products and of the starting materials was carried out by gas chromatography. The type of catalyst used, the temperature, the space velocity (WHSV), the conversion and the selectivity are stated in the Tables below.

The following catalysts were employed:

Catalyst A

The borosilicate zeolite was prepared in a hydrothermal synthesis from 640 g of $SiO_2$ (highly disperse silica), 122 g of $H_3BO_3$ and 8000 g of an aqueous 1,6-hexanediamine solution (weight ratio 50:50) at 170° C. under autogenous pressure, in a stirred autoclave. The crystalline reaction product was filtered off, washed thoroughly, dried at 100° C. for 24 hours and then calcined at 500° C. for 24 hours. A borosilicate zeolite of the pentasil type, containing 94.2% by weight of $SiO_2$ and 2.3% by weight of $B_2O_3$, was obtained.

The borosilicate zeolite was molded with boehmite in a weight ratio of 60:40 to give 2 mm extrudates, and the latter were dried at 110° C. for 16 hours and calcined at 500° C. for 24 hours.

Catalyst B

The extrudates of catalyst A were treated with ammoniacal $Pd(NO_3)_2$ solution. The Pd content of the catalyst was 3.3% by weight.

Catalyst C

The molded borosilicate zeolite described under catalyst A was impregnated with $Ni(NO_3)_2.6H_2O$. The Ni content of the ready-prepared catalyst was 3.5% by weight.

Catalyst D

The borosilicate zeolite as described for catalyst A was converted in the absence of a binder to 2 mm extrudates, and the latter were dried at 110° C. for 16 hours and calcined at 500° C. for 16 hours. 100 g of these extrudates were impregnated with a solution containing Pd and Ce. The solution used was composed of 15.5 g of an 11% strength ammoniacal Pd(NO$_3$)$_2$ solution and 13.3 g of Ce(NO$_3$)$_3$.6H$_2$O in 80 g of H$_2$O. The supernatant liquid was freed from residual water, after which the product was dried at 130° C. for 2 hours and calcined at 540° C. for 2 hours. The Pd content of the catalyst was 1.5% by weight and the Ce content was 3.5% by weight.

Catalyst E

An aluminosilicate zeolite of the pentasil type was prepared under hydrothermal conditions, under autogenous pressure and at 150° C., from 650 g of highly disperse SiO$_2$ and 203 g of Al$_2$(SO$_4$)$_3$.18H$_2$O in 10 kg of an aqueous 1,6-hexanediamine solution (weight ratio 50:50) in a stirred autoclave. The crystalline reaction product was filtered off, washed thoroughly, dried at 110° C. for 24 hours and then calcined at 500° C. for 24 hours. This aluminosilicate zeolite contained 91.6% by weight of SiO$_2$ and 4.6% by weight of Al$_2$O$_3$.

This zeolite was converted to 2 mm extrudates by molding, and the extrudates were dried at 100° C. for 16 hours and calcined at 500° C. for 16 hours.

Catalyst F

Catalyst F was obtained by impregnating catalyst E with an 11% strength aqueous Pd(NO$_3$)$_2$ solution. The Pd content of the catalyst calcined at 540° C. was 3.2% by weight.

Catalyst G

Catalyst G was obtained by the method described for catalyst D, except that the aluminosilicate zeolite described under catalyst E was employed. The Pd content was 1.5% by weight and the Ce content was 3.6% by weight.

TABLE 1

Conversion of α-limonene and a α- and β-pinene

| Example | Starting material | Catalyst | Temperature °C. | WHSV h$^{-1}$ | Conversion % | Selectivity[a] in % p-cymene | MIC[b] |
|---|---|---|---|---|---|---|---|
| 1 | α-limonene | A | 200 | 2.4 | 100 | 20.8 | 16.1 |
| 2 | " | B | 200 | 2.4 | 100 | 70.0 | 13.0 |
| 3 | " | C | 200 | 2.4 | 100 | 47.5 | 4.2 |
| 4 | " | D | 150 | 1.7 | 100 | 75.2 | 24.4 |
| 5 | " | D | 200 | 1.7 | 100 | 86.6 | 11.4 |
| 6 | " | E | 200 | 2.4 | 100 | 44.5 | 12.8 |
| 7 | " | F | 200 | 2.4 | 100 | 73.5 | 11.0 |
| 8 | " | G | 200 | 2.4 | 100 | 73.7 | 11.7 |
| 9 | α-pinene | B | 200 | 2.0 | 96.8 | 57.0 | 11.4 |
| 10 | β-pinene | B | 200 | 2.4 | 99.0 | 55.1 | 14.3 |

[a]based on converted starting material
[b]MIC = methylisopropylcyclohexane/methylisopropylcyclohexene Toluene and xylene may be obtained as further by-products.

TABLE 2

Conversion of vinylcyclohexene

| Example | Catalyst | Temperature °C. | WHSV h$^{-1}$ | Conversion % | Selectivity in %[a] Ethylbenzene | Ethylcyclohexane/ ethylcyclohexene |
|---|---|---|---|---|---|---|
| 11 | B | 200 | 2.4 | 100 | 70.7 | 9.2 |
| 12 | D | 200 | 1.0 | 100 | 82.8 | — |

[a]based on converted vinylcyclohexene

We claim:
1. In a process for the preparation of an alkylbenzene by converting an alkylcyclohexene, an alkylidenecyclohexene and/or an alkenylcyclohexene or an alkyl- or an alkenylcyclohexadiene in the presence of a catalyst, the improvement which comprises:
carrying out the conversion with an acidic zeolite catalyst having the pentasil structure and in the gas phase or liquid phase.
2. A process as claimed in claim 1, wherein cyclohexenes and/or cyclohexadienes which are substituted at a carbon atom by alkenyl of 2 to 10 carbon atoms and may carry an alkyl group of 1 to 4 carbon atoms on another carbon atom are converted.
3. A process as claimed in claim 1, wherein the alkenylcyclohexene of the formula (I)

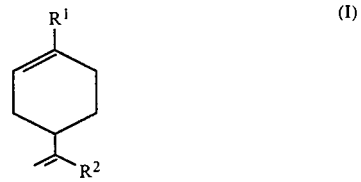

where R$^1$ and R$^2$ independently of one another are each hydrogen or a low molecular weight alkyl group, is converted.
4. A process as claimed in claim 1, wherein a mono- or bicyclic monoterpene of the empirical formula C$_{10}$H$_{16}$, is converted alone or in the form of an isomer mixture.
5. A process as claimed in claim 1, wherein the reaction is carried out in the liquid phase at from 30° to 300° C.
6. A process as claimed in claim 1, wherein the catalyst used is a borosilicate zeolite having the pentasil type.
7. A process as claimed in claim 1, wherein the catalyst used is an aluminosilicate zeolite having the pentasil structure.
8. A process as claimed in claim 1, wherein the catalyst used is an iron silicate zeolite having the pentasil type.
9. A process as claimed in claim 1, wherein the catalyst used is a pentasil zeolite doped with at least one metal selected from the group consisting of transition metals of Group VIII of the Periodic System and rare earth metals.
10. A process as claimed in claim 9, wherein Ni, Pd, Ce or a mixture of these is used as a dopant.
11. A process as claimed in claim 1, wherein the reaction is carried out in the gas phase at from 100° to 500° C.
12. A process as claimed in claim 4, wherein the compound being converted is selected from the group consisting of α-limonene, α-pinene and β-pinene.
13. A process as claimed in claim 1, wherein the compound being converted is vinylcyclohexene.
14. A process as claimed in claim 1, wherein the reaction is carried out in the liquid phase at from 50° to 200° C.
15. A process as claimed in claim 1, wherein the reaction is carried out in the gas phase at from 200° to 400° C.

* * * * *